United States Patent [19]

Usui et al.

[11] 4,220,356
[45] Sep. 2, 1980

[54] RECORDING MATERIALS CONTAINING CHROMENOINDOLES

[75] Inventors: Hideo Usui; Sadao Ishige, both of Minami-ashigara; Keiso Saeki, Fujinomiya, all of Japan

[73] Assignee: Fuji Photo Film Co., Ltd., Minami-ashigara, Japan

[21] Appl. No.: 16,465

[22] Filed: Mar. 1, 1979

Related U.S. Application Data

[63] Continuation-in-part of Ser. No. 827,053, Aug. 23, 1977, abandoned.

[30] Foreign Application Priority Data

Aug. 24, 1976 [JP] Japan .................. 51-100971

[51] Int. Cl.$^2$ .................. B41M 5/16; B41M 5/22
[52] U.S. Cl. .................. 282/27.5; 260/319.1; 427/151; 428/307; 428/537; 428/914
[58] Field of Search .................. 106/21; 282/27.5; 260/313.1, 319.1, 326.14 R, 326.15, 326.16, 326.5 B; 427/151; 428/307, 411, 537, 913, 914; 252/316; 544/81, 142; 546/187

[56] References Cited

U.S. PATENT DOCUMENTS

| | | | |
|---|---|---|---|
| 3,509,174 | 4/1970 | Lin | 282/27.5 |
| 3,619,239 | 11/1971 | Osada et al. | 428/307 |
| 3,702,244 | 11/1972 | Bloom et al. | 96/3 |
| 3,929,829 | 12/1975 | Borror | 260/326.15 |
| 3,995,088 | 12/1976 | Garner et al. | 428/323 |
| 4,123,439 | 10/1978 | Balli et al. | 260/326.5 B |

*Primary Examiner*—Bruce H. Hess
*Attorney, Agent, or Firm*—Sughrue, Rothwell, Mion, Zinn and Macpeak

[57] ABSTRACT

A chromenoindole derivative of the following general formula (I):

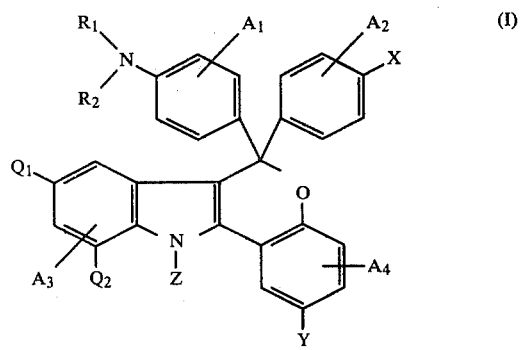

wherein $R_1$ and $R_2$, which may be the same or different, each represents an alkyl group, an alkyl group substituted with one or more of a cyano group, a halogen atom or an alkoxy group, an aralkyl group, a phenyl group or a phenyl group substituted with one or more of an alkyl group or a halogen atom; X represents a hydrogen atom, an alkoxy group, a dialkylamino group, an alkylarylamino group, an alkylaralkylamino group, a diaralkylamino group, an acylamino group, a halogen atom or an alkyl group; Y represents a hydrogen atom, an alkyl group, a halogen atom, an alkoxy group of a nitro group; Z represents an acyl group, or a sulfonyl group; $Q_1$ and $Q_2$, which may be the same or different, each represents a hydrogen atom, a lower alkyl group or a halogen atom; and $A_1$, $A_2$, $A_3$ and $A_4$, which may be the same or different, each represents a halogen atom, an alkyl group or an alkoxy group; which upon contact with an electron acceptor material forms a color with superior light fastness and which is useful as a color former in various recording materials such as pressure-sensitive recording sheets, thermosensitive recording sheets, electrothermosensitive recording sheets, and photosensitive recording sheets.

12 Claims, No Drawings

RECORDING MATERIALS CONTAINING CHROMENOINDOLES

This application is a continuation-in-part application of Ser. No. 827,053, filed Aug. 23, 1977.

BACKGROUND OF THE INVENTION

1. Field of the Invention

This invention relates to recording materials, especially pressure-sensitive copying sheets, thermosensitive recording sheets, electrothermosensitive recording sheets and photosensitive recording sheets which provide colored images having superior light fastness, and to a chromenoindole derivative useful therein.

2. Description of the Prior Art

A great many methods have been devised to record information transmitted using energy such as pressure, heat, light or electricity, but very few of these methods have been used practically.

Recording methods of commercially avilable pressure-sensitive copying sheets, thermosensitive recording sheets and electrothermosensitive recording sheets utilize the fact that an organic electron donor compound (also called a "color former"), which is a substantially colorless organic compound that forms a color upon reaction with an electron acceptor material (also called a "color developer"), which is a compound acting as a Brønsted acid or a Lewis acid, for example, clay minerals such as active terra alba; organic acids such as phenols, organic carboxylic acids or organic sulfonic acids; salts of phenols, organic carboxylic acids or organic sulfonic acids with metals such as aluminum, zinc, nickel or tin; inorganic acids such as hydrohalic acids, boric acid, silicic acid, phosphoric acid, sulfuric acid, nitric acid and perchloric acid; and halides of aluminum, zinc, nickel, tin, titanium and boron, upon contact with each other by application of pressure, heating or passing of an electric current therethrough result in the formation of a color (with at least one of the color former and the color developer being in the form of a solution, a liquid or a gas during contact).

Other than silver salt photographic materials, only diazo photosensitive sheets are used as inexpensive photosensitive recording sheets. Also, methods have been devised for photosensitive recording sheets which are based on a combination of a color former, as an electron donor material, and a compound which generates an acid, as an electron acceptor material, upon exposure to light. Such methods are described, for example, in Japanese Patent Publication Nos. 21118/63, 10550/70, 6212/74 and 28449/74 and Japanese Patent Application (OPI) Nos. 32532/73, 80120/75, 87317/75 and 12622/75.

Color formers which form color upon intimate contact with electron acceptor materials have been studied heretofore mainly as color formers for pressure-sensitive copying sheets. There are many requirements for color formers for use in pressure-sensitive copying sheets, among which are:

(1) they should be substantially colorless compounds;

(2) they should almost instantaneously form deep colors upon intimate contact with electron acceptor materials;

(3) they should be easily soluble in certain organic solvents;

(4) they should not sublime;

(5) they should not decompose nor form a color upon exposure to light, heat, moisture in the atmosphere, etc., until they come into intimate contact with electron acceptor materials;

(6) the color images formed upon contact with electron acceptor materials should be resistant to light, heat, moisture in the atmosphere, etc.;

(7) they should be non-toxic and non-polluting; and (8) they should be capable of being synthesized at low cost on a commercial scale.

No color former has yet met all of these requirements, and suitable techniques for use have been devised, for example, by combining at least two color formers or by selecting appropriate electron acceptor materials.

Since color formers for pressure-sensitive copying sheets should meet a large number of requirements and these requirements are very important, all color formers that can be used for pressure-sensitive copying sheets can be used as color formers in thermosensitive recording sheets, electrothermosensitive recording sheets, and photosensitive recording sheets which are based on the utilization of color formation by the reaction of electron donor materials and electron acceptor materials. The color formers presently used for thermosensitive recording sheets and electrothermosensitive recording sheets now on the market are color formers for pressure-sensitive copying sheets. The color formers for photosensitive recording sheets which are described in the above-cited Japanese Patents are mostly those known as color formers for pressure-sensitive copying papers. It has been suggested to utilize color formers for pressure-sensitive copying papers in ultrasonic recording sheets (e.g., as disclosed in French Pat. No. 2,120,922), electron beam recording materials, electrostatic recording sheets (e.g., as disclosed in Japanese Patent Publication No. 3932/74), formation of color images on a light-sensitive printing plate (e.g., as disclosed in Japanese Patent Application (OPI) No. 12104/73), impression-stamping materials (e.g., as disclosed in Japanese Patent Publication No. 10766/72), typewriter ribbons (e.g., as disclosed in Japanese Patent Application (OPI) No. 3713/74), ball-point pen inks (e.g., as disclosed in Japanese Patent Application (OPI) No. 83924/73), and crayons (e.g., as disclosed in U.S. Pat. No. 3,769,045).

A large number of patent applications have been filed regarding color formers for pressure-sensitive copying sheets. However, none of the color formers thus far discovered completely meet requirements (2), (5) and (6) described above, let alone all of the eight requirements described above.

Crystal violet lactone (A):

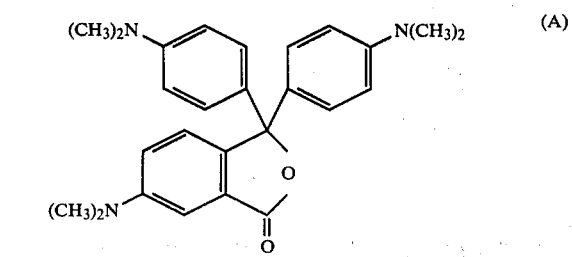

now used as a blue color former meets requirements (2) and (5), but not requirement (6). Therefore, the practice is to use crystal violet lactone together with N-benzoyl leucomethylene blue (B):

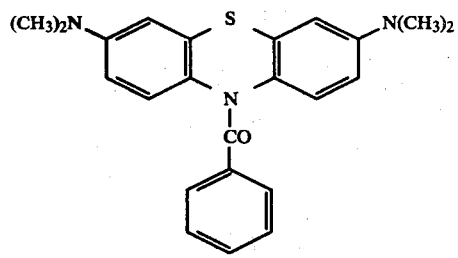
(B)

which meets requirement (6), but not requirements (2) and (5). However, since different colors are formed by (A) and (B), another color former must be added for adjustment of color, and this is economically disadvantageous. Furthermore, crystal violet lactone has the defect of coloration when exposed to sunlight before use.

As red and black color formers, fluoran type color formers, of which the compound (C) below is typical, are used.

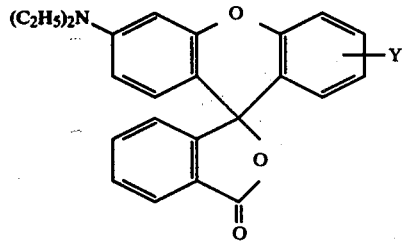
(C)

Fluoran type color formers have the disadvantage that the color densities, colors and light fastness characteristics of colors formed by these color formers vary depending on the type of the electron acceptor material, especially a difference is observed when active terra alba and a phenolic resin is used. The color density of the dye formed by contact with active terra alba is high but the light fastness of the dye is poor. On the other hand, a dye formed by contact with a phenolic resin generally has good light fastness, but a low color density. Thus, an ideal electron acceptor material for these fluoran color formers has not been discovered.

In U.S. Pat. No. 4,123,439, it is disclosed that the chromenoindole compounds of the following general formula are useful as color formers.

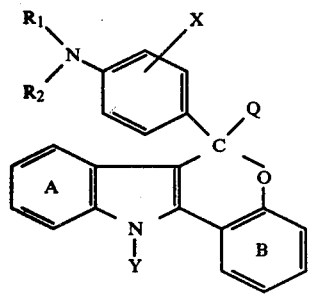
(1)

wherein $R_1$ and $R_2$ independently of one another represent hydrogen, alkyl which has at most 12 carbon atoms and is unsubstituted or substituted by halogen, hydroxyl, cyano or lower alkoxy; cycloalkyl, phenyl, benzyl, or phenyl or benzyl which are substituted by halogen, lower alkyl or lower alkoxy, or $R_1$ and $R_2$, together with the nitrogen atom which links them, represent a 5-membered or 6-membered heterocyclic radical, Q is hydrogen, lower alkyl, phenyl, benzyl or the groups of the formulae (1a) or (1b)

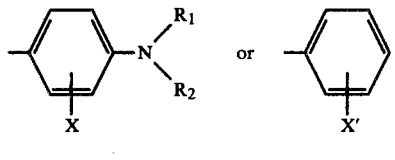

(1a)    (1b)

X and X' each represents hydrogen, halogen, lower alkyl or lower alkoxy, Y represents hydrogen, alkyl of 1 to 12 carbon atoms, phenyl or benzyl and the rings A and B independently of one another are unsubstituted or substituted by halogen, nitro, lower alkyl, lower alkoxy, phenoxy, amino or amino substituted by lower alkyl, phenyl or benzyl.

However, in the chromenoindole compounds above, when Q is phenyl or substituted phenyl, ring cleavage of the chromen ring easily occurs and, therefore, formation of fog easily occurs. Further, the chromenoindole compounds wherein Q is phenyl or substituted phenyl easily forms a color in a polar solvent such as alcohol and also easily forms a color in a microcapsulation process. These defects cause bad problems in a preparation of pressure-sensitive recording paper.

Color formers used for thermosensitive recording sheets and electrothermosensitive recording sheets are similar to those used for pressure-sensitive copying sheets, but have a problem with respect to light fastness and fogging (coloration of the background) before color formation. The main reason for this is that these formers do not sufficiently meet requirements (5) and (6) above.

Photosensitive recording sheets are obtained by coating a compound (for example, organic halogen compounds such as carbon tetrachloride, $\alpha,\alpha,\alpha$-tribromoacetophenone, hexachloroethane, iodoform, 2-tribromomethylpyridine and trichloromethylsulfonylbenzene; o-quinonediazide type compounds such as those disclosed in Japanese Patent Application (OPI) No. 12104/73; and phenol esters of carboxylic acids or sulfonic acids which will undergo a Fries rearrangement by light) which will form an electron acceptor material (for example, hydrogen halides such as hydrogen chloride, hydrogen bromide or hydrogen iodide, carboxylic acids, sulfonic acids, and phenols) by light, and an electron donating color former (for example, a color former for pressure-sensitive copying sheets) on a support such as paper or a synthetic resin film together with a suitable binder. However, conventional color formers give rise to colors with poor light fastness and are subject to considerable fogging before color formation. Furthermore, the color density of the color at the light exposed portion is low.

In application to ultrasonic recording sheets, electron beam recording sheets, electrostatic recording sheets, light-sensitive printing plates, impression-stamping materials, typewriter ribbons, ball-point pen inks, and crayons, the colors formed have insufficient color densities and fastness because conventional color formers do not sufficiently meet requirements (2), (5) and (6). Moreover, these color formers have unsatisfactory storage stability and fogging before use and poor color formation during use result.

SUMMARY OF THE INVENTION

Therefore, investigations on color formers for pressure-sensitive copying sheets have been made in order to remedy the various defects of recording materials utilizing color formation by the reaction of an electron donor material and an electron acceptor material.

Accordingly, an object of this invention, therefore, is to provide recording materials which provide colored images with improved light fastness (for example, pressure-sensitive copying sheets, thermosensitive recording sheets, electrothermosensitive recording sheets, light-sensitive recording sheets, ultrasonic recording sheets, electron beam recording materials, electrostatic recording sheets, light-sensitive printing plates, impression-stamping materials, typewriter ribbons, ball-point pen inks, and crayons).

Another object of this invention is to provide recording materials of the above-described type which have superior storage stability before use, whose color forming properties are not deteriorated and in which fog does not occur.

The objects of this invention are achieved by a recording material in which a color is formed by contact of an indolochromene derivative of the general formula (I) below as a color former with an electron acceptor material.

The present invention thus provides a recording material capable of forming a color by contacting, with an electron acceptor material, at least one chromenoindole derivative of the general formula (I):

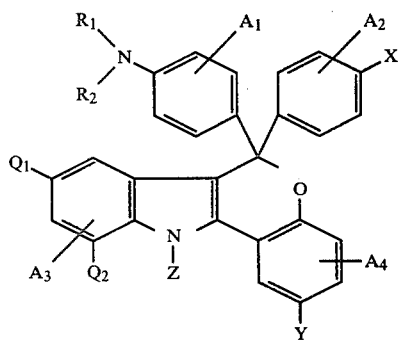

wherein $R_1$ and $R_2$, which may be the same or different, each represents an alkyl group (e.g., having 1 to 7 carbon atoms such as a methyl group, an ethyl group, a propyl group, a butyl group, etc.), a substituted alkyl group (which may be substituted with one or more of a cyano group, a halogen atom (e.g., a chlorine atom, a bromine atom, etc.) or an alkoxy group (e.g., having 1 to 5 carbon atoms such as a methoxy group, an ethoxy group, a butoxy group, etc.)), an aralkyl group (e.g., having 7 to 11 carbon atoms such as a benzyl group, etc.), or a phenyl group (which may be substituted with one or more of an alkyl group (e.g., having 1 to 3 carbon atoms such as a methyl group, an ethyl group, a propyl group, etc.), a halogen atom (e.g., a chlorine atom, a bromine atom, etc.), etc.); X represents a hydrogen atom, an alkoxy group (e.g., having 1 to 5 carbon atoms such as a methoxy group, an ethoxy group, a butoxy group, etc.), a dialkylamino group (e.g., having 1 to 5 carbon atoms in the alkyl moiety thereof such as a dimethylamino group, a diethylamino group, etc.), an alkylarylamino group (e.g., having 1 to 5 carbon atoms in the alkyl moiety thereof such as an N-ethyl-N-(4-chlorophenyl)amino group, etc.), an alkylaralkylamino group (e.g., having 7 to 11 carbon atoms in the aralkyl moiety thereof and 1 to 5 carbon atoms in the alkyl moiety thereof such as an ethylbenzylamino group, etc.), a diaralkylamino group (e.g., having 7 to 11 carbon atoms in the aralkyl moiety thereof such as a dibenzylamino group, etc.), an acylamino group (such as an acetylamino group, a benzoylamino group, etc.), a halogen atom (e.g., a chlorine atom, a bromine atom, etc.) or an alkyl group (e.g., having 1 to 5 carbon atoms such as a methyl group, an ethyl group, etc.); Y represents a hydrogen atom, an alkyl group (e.g., having 1 to 5 carbon atoms such as a methyl group, an ethyl group, etc.), a halogen atom (e.g., a chlorine atom, a bromine atom, etc.), an alkoxy group (e.g., having 1 to 5 carbon atoms such as a methoxy group, an ethoxy group, a butoxy group, etc.) or a nitro group; Z represents an acyl group or a sulfonyl group. The acyl group includes an alkylcarbonyl group, an arylcarbonyl group, an alkoxycarbonyl group, and a carbamoyl group. The sulfonyl group includes an alkylsulfonyl group, an arylsulfonyl group and a sulfamoyl group. The preferable examples of an acyl group are an alkylcarbonyl group (e.g., having 1 to 7 carbon atoms in the alkyl moiety thereof such as an acetyl group, a butyryl group, etc.), an arylcarbonyl group (e.g., having 6 to 11 carbon atoms in the aryl moiety thereof such as a benzoyl group, a toluoyl group, etc.), alkoxycarbonyl group (e.g., having 1 to 7 carbon atoms in the alkyl moiety thereof such as methoxycarbonyl group, etc.), aryloxycarbonyl group (e.g., having 6 to 11 carbon atoms in the aryl moiety thereof such as phenoxycarbonyl group, etc.), carbamoyl group (e.g., having 1 to 10 carbon atoms such as a diethylcarbamoyl group, a phenylcarbamoyl group, etc.). The preferable examples of a sulfonyl group are alkylsulfonyl group (e.g., having 1 to 7 carbon atoms in the alkyl moiety thereof such as a methanesulfonyl group, etc.), arylsulfonyl group (e.g., having 6 to 11 carbon atoms in the aryl moiety such as a p-toluenesulfonyl group). $Q_1$ and $Q_2$, which may be the same or different, each represents a hydrogen atom, a lower alkyl group (e.g., having 1 to 5 carbon atoms such as a methyl group, an ethyl group, a propyl group, a butyl group, etc.) or a halogen atom (e.g., a chlorine atom, a bromine atom, etc.); and $A_1$, $A_2$, $A_3$ and $A_4$, which may be the same or different, each represents a halogen atom (e.g., a chlorine atom, a bromine atom, etc.), an alkyl group (e.g., having 1 to 3 carbon atoms such as a methyl group, an ethyl group, etc.), an alkoxy group (e.g., having 1 to 5 carbon atoms such as a methoxy group, an ethoxy group, a butoxy group, etc.), etc.

DETAILED DESCRIPTION OF THE INVENTION

The chromenoindole derivatives used in this invention of the general formula (I) above are novel compounds, and are usually colorless to slightly colored powdery crystals. When contacted with electron acceptor materials, they immediately form very deep shades of blue to violet or blackish blue colors. The dyes formed are discolored to a far less extent upon exposure to light than are dyes formed from color formers which are now in use and form blue to violet colors, such as crystal violet lactone. Thus, the chromenoindole derivatives of the general formula (I) are very advantageous for storage as records for long periods of time. Furthermore, these compounds before color formation are stable and withstand storage for long periods of time, and, therefore, recording materials using these compounds as color formers can be fully used even after they have been stored for long periods of time. Moreover, the color shade of these chromenoindole derivatives changes only slightly even when the types of electron donor materials change. This is advantageous in predetermining the color of an image to be formed by a recording material.

Typical examples of chromenoindole derivatives of the general formula (I) above are set forth below. However, it should be understood that the invention is in no way to be construed as being limited to the exemplified compounds set forth below:

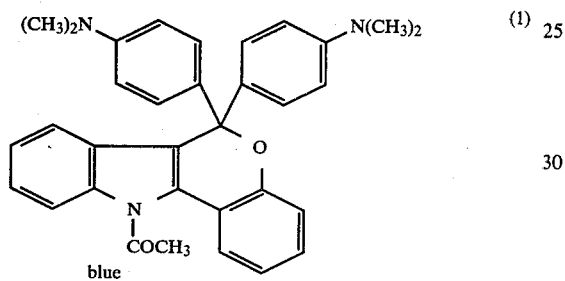
(1)
blue

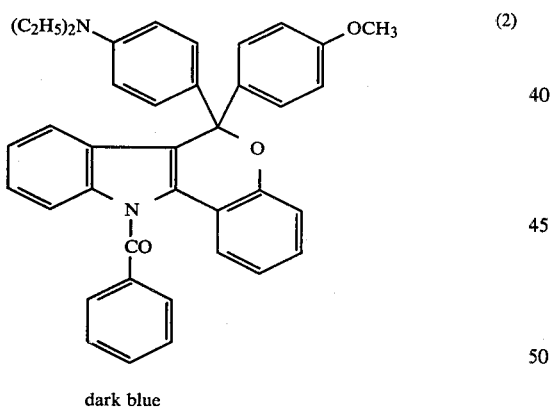
(2)
dark blue

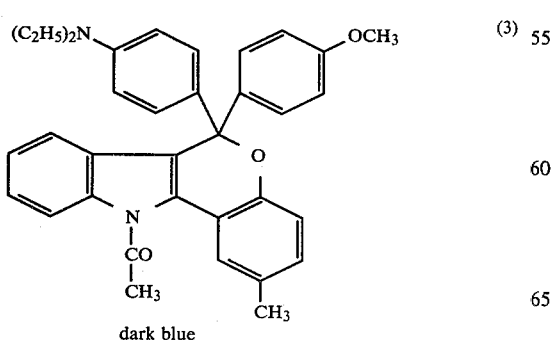
(3)
dark blue

-continued

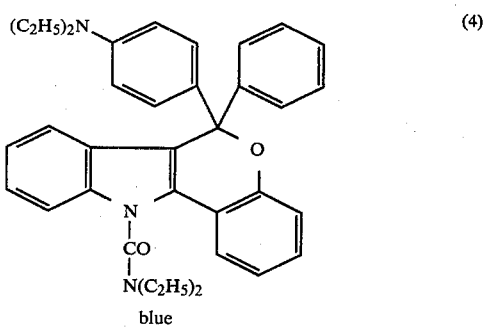
(4)
blue

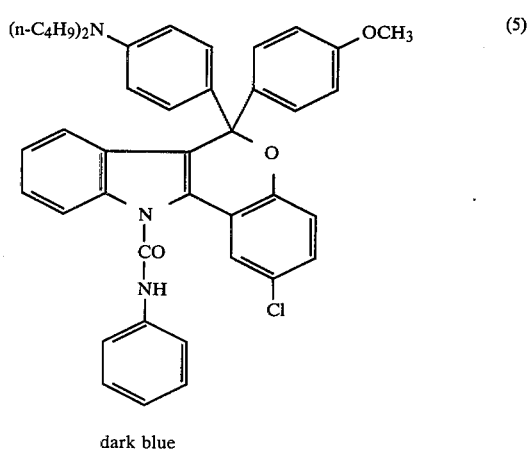
(5)
dark blue

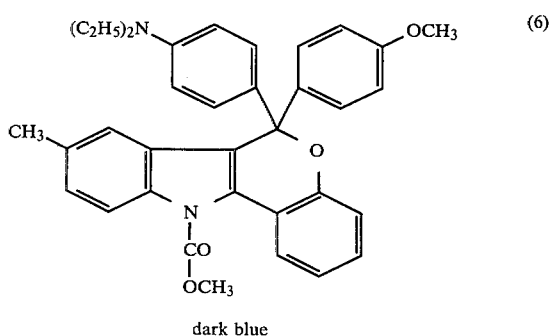
(6)
dark blue

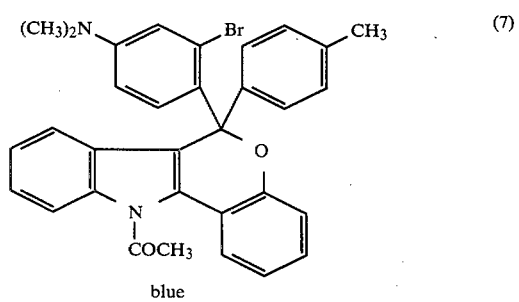
(7)
blue

-continued

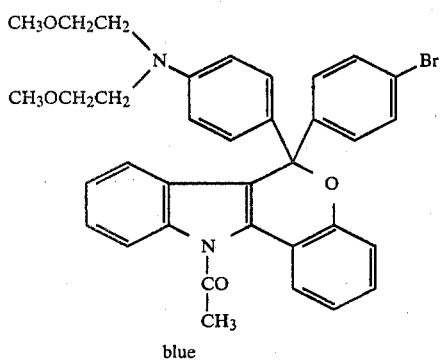
(8) blue

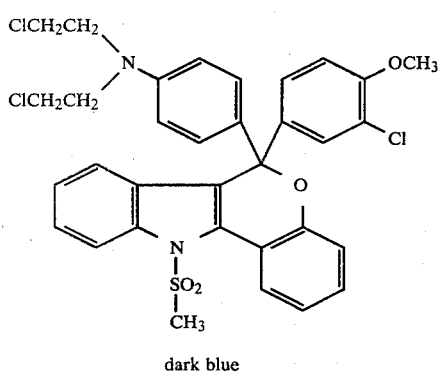
(9) dark blue

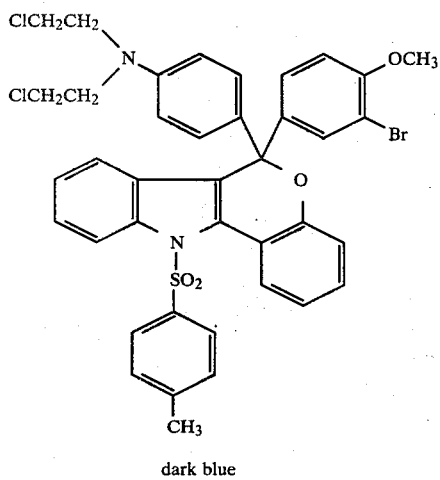
(10) dark blue

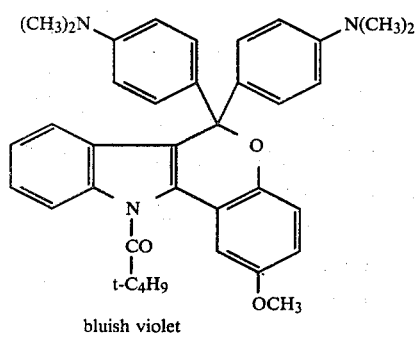
(11) bluish violet

-continued

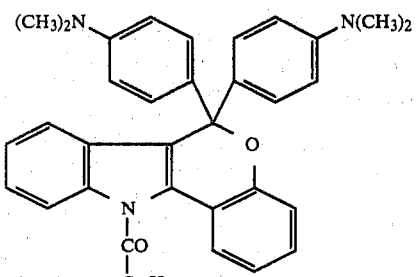
(12) blue

The colors indicated above for the compounds of this invention are those obtained on contact with a color developer.

The chromenoindole derivatives used in this invention can be synthesized by the method schematically shown below.

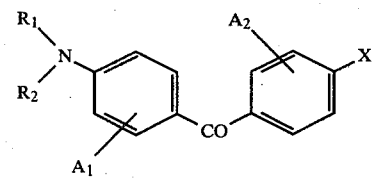
Compound of the general formula (II)

+

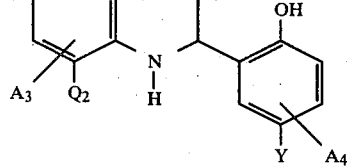
Compound of the general formula (III)

↓

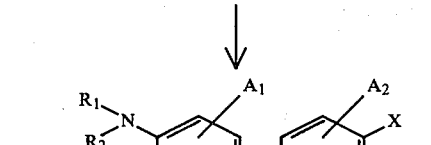
(IV)

↓ + acylating agent

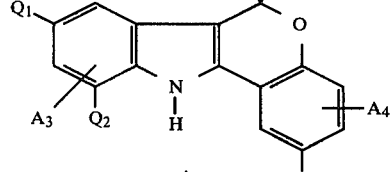
Compound of the general formula (I)

In the general formulae (II), (III) and (IV), $R_1$, $R_2$, X, Y, $Q_1$, $Q_2$, $A_1$, $A_2$, $A_3$ and $A_4$ each has the same meaning as defined with regard to the general formula (I).

More specifically, a benzophenone derivative of the general formula (II) is dissolved or dispersed in a solvent which does not react with a condensing agent as described below (for example, halogenated hydrocabons such as chloroform, methylene dichloride, trichloroethane or dichloroethane; aromatic hydrocarbons such as benzene or toluene; ethers such as diethyl ether, dioxane or tetrahydrofuran; or dimethyl sulfoxide). A condensing agent is added, and the mixture is stirred (optionally while heating the mixture at about 40° to about 100° C.). The condensing agent activates the carbonyl group to induce a Friedel-Crafts reaction. Suitable condensing agents which can be used include Friedel-Crafts type condensing agents (such as thionyl chloride, zinc chloride, aluminum chloride, titanium tetrachloride, and tin chloride), and tri- to pentavalent inorganic phosphorus compounds (such as phosphorus oxychloride, phosphorus pentachloride, and phosphorus trichloride). Some of these condensing agents can act as a solvent (for example, phosphorus oxychloride, phosphorus trichloride, and thionyl chloride) and in this case, the use of the above-described solvent is not required. A suitable amount of the condensing agent is about 1 to about 10 times by weight to the weight of the benzophenone derivative of the general formula (II).

Then, an indole derivative of the general formula (III) is added to the reaction system to produce a chromenoindole derivative of the general formula (IV). The benzophenone derivative of the general formula (II) and the indole derivative of the general formula (III) are generally employed in equimolar proportions, but no adverse effect on the reaction arises even if one of the reactants is present in a molar excess. The reaction is carried out at about 25 to about 150° C. (with the reaction time being about 30 minutes to about 8 hours although the reaction time will differ depending upon the reaction temperature) at atmospheric pressure. The compound of the general formula (IV) is converted to the chromenoindole derivative of the general formula (I) by reaction with an acylating agent or a sulfonylating agent at about 0° to about 60° C.

Typical examples of the benzophenone derivatives of the general formula (II) which can be employed are set forth below:

4,4'-bis-Dimethylaminobenzophenone
4,4'-bis-Diethylaminobenzophenone
4,4'-bis-Dibutylaminobenzophenone
4,4'-bis-Dibenzylaminobenzophenone
4,4'-bis(N-Ethyl-N-p-tolylamino)benzophenone
4,4'-bis(N-Benzyl-N-ethylamino)benzophenone
4-Dimethylaminobenzophenone
4-Diethylaminobenzophenone
4-Dibutylaminobenzophenone
4-Diethylamino-4'-methylbenzophenone
4-Dibutylamino-4'-methylbenzophenone
4-Dimethylamino-4'-chlorobenzophenone
4-Diethylamino-4'-bromobenzophenone
4-Dimethylamino-4'-methoxybenzophenone
4-Diethylamino-4'-methoxybenzophenone
4-Dibutylamino-4'-methoxybenzophenone
4-Dimethylamino-4'-ethoxybenzophenone
4-Diethylamino-4'-ethoxybenzophenone
4-Dibutylamino-4'-ethoxybenzophenone
4-Dimethylamino-4'-propoxybenzophenone
4-Diethylamino-4'-propoxybenzophenone
4-Dibutylamino-4'-propoxybenzophenone
4-(N-Ethyl-N-p-tolylamino)-4'-methoxybenzophenone
4-Dimethylamino-4'-acetaminobenzophenone
4-Diethylamino-4'-acetaminobenzophenone
4-Dibutylamino-4'-acetaminobenzophenone
4-Di($\beta$-cyanoethyl)amino-4'-ethoxybenzophenone
4-Di($\beta$-chloroethyl)amino-4'-methoxybenzophenone
4-Di($\beta$-cyanoethyl)amino-4'-chlorobenzophenone
4-Di($\beta$-cyanoethyl)amino-4'-butoxybenzophenone
4-Di($\beta$-chloroethyl)amino-4'-butoxybenzophenone
4-Di($\beta$-methoxyethyl)amino-4'-chlorobenzophenone
4-Di($\beta$-methoxyethyl)amino-4'-bromobenzophenone
4-Di($\beta$-methoxyethyl)amino-4'-butoxybenzophenone
2-Methyl-4-diethylamino-4'-methoxybenzophenone
2-Methyl-4-diethylamino-4'-ethoxybenzophenone
2-Chloro-4-di($\beta$-cyanoethyl)amino-4'-ethoxybenzophenone
2-Chloro-4-diethylamino-4'-methoxybenzophenone
2-Bromo-4-dimethylamino-4'-methylbenzophenone
2-Bromo-4-diethylamino-4'-methoxybenzophenone
4-Di($\beta$-chloroethyl)amino-3'-chloro-4'-methoxybenzophenone
4-Di($\beta$-chloroethyl)amino-3'-bromo-4'-methoxybenzophenone These examples given above are preferred species, and the invention is not to be construed as being limited to them.

Typical examples of indole derivatives of the general formula (III) which can be used include the compounds set forth below:

2-(2-Hydroxyphenyl)indole
2-(2-Hydroxy-5-methylphenyl)indole
2-(2-Hydroxy-5-chlorophenyl)indole
2-(2-Hydroxy-5-methoxyphenyl)indole
2-(2-Hydroxyphenyl)-5-methylindole
2-(2-Hydroxyphenyl)-5-chloroindole
2-(2-Hydroxyphenyl)-7-methylindole
2-(2-Hydroxy-5-nitrophenyl)indole
2-(2-Hydroxyphenyl)-5-bromoindole These compounds set forth above are preferred species and the invention is not to be construed as being limited to them.

Examples of suitable acylating agents which can be used are acid anhydrides such as acetic anhydride, propionic anhydride and benzoic anhydride; and acid halides such as acetyl chloride, propionyl chloride, butyryl chloride, pivaloyl chloride, valeryl chloride, octanoyl chloride, decanoyl chloride, dodecanoyl chloride, tetradecanoyl chloride, hexadecanoyl chloride, octadecanoyl chloride, allyl bromide, benzoyl chloride, and anisoyl chloride. Suitable sulfonylating agents include methanesulfonyl chloride, benzenesulfonyl chloride, and p-toluenesulfonyl chloride.

Typical methods for the synthesis of the compounds of the general formula (I) are shown below. Unless otherwise indicated, all parts, percents, ratios and the like are by weight.

SYNTHESIS EXAMPLE (1) Synthesis of 6,6-bis(p-dimethylaminophenyl)-6,11-dihydro-[1]benzopyrano[4,3-b]indole

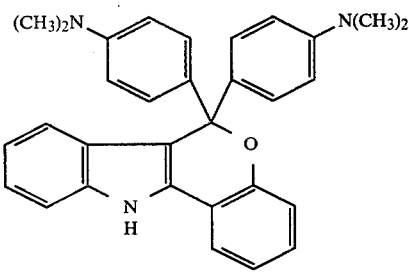

7.7 g of 4,4'-bisdimethylaminobenzophenone was dissolved in 50 ml of chloroform, and the solution was stirred. Phosphorus oxychloride (5 g) and 10 ml of chloroform were added thereto, and the mixture was stirred for 30 minutes at room temperature (about 20°–30° C.). Then, 6 g of 2-(2'-hydroxyphenyl)indole was added thereto, and the mixture was stirred at room temperature for 3 hours. The mixture was heated under reflux for an additional 2 hours. The heated mixture was cooled to room temperature, and poured into ice water, and neutralized with an aqueous solution of sodium hydroxide. Furthermore, 200 to 300 ml of chloroform was added for extraction. The chloroform layer was washed with water, dried, and distilled under reduced pressure to remove the chloroform. The remaining oily substance was dissolved in a small amount of methanol by heating, and the solution was cooled. The crystals precipitated were separated by filtration, and dried to obtain 4 g of the objective compound having a melting point of 165° to 168° C.

(2) Synthesis of Compound (1)

2 g of 6,6-bis(p-dimethylaminophenyl)-6,11-dihydro-[1]benzopyrano[4,3-b]indole was reacted with 5 g of acetic anhydride under heating, and the excess of the acetic anhydride and acetic acid formed by the reaction were distilled off under reduced pressure. The remaining oily substance was dissolved in a small amount of methanol, and cooled to precipitate white crystals. Filtration and drying of the crystals gave 2 g of Compound (1) having a melting point of 237° to 239° C.

Compound (1) formed a blue color upon contact with acetic acid.

The electron acceptor materials which are used in this invention are also called color developers, and are compounds which can act as Brønsted acids or Lewis acids. Examples of electron acceptor materials are clay minerals such as active terra alba, acid terra alba, attapulgite and montmorillonite; phenols such as p-phenylphenol, o-phenylphenol, o-ethylphenol, p-ethylphenol, p-butylphenol, 2,4-dibutylphenol, o-cresol, m-cresol, p-cresol, o-chlorophenol, p-chlorophenol, o-benzylphenol, p-benzylphenol, xylenol, thymol, resorcinol, hexylresorcinol, α-naphthol, β-naphthol, 4,4'-isopropylidene diphenol and 2,2'-methylenebisphenol; phenolic resins, organic acids such as organic carboxylic acids and organic sulfonic acids; metal salts of organic acids such as organic acid salts of Al, Zn, Ni and Sn, especially aluminum 3,5-dibutyl-salicylate, zinc 3,5-dibutylsalicylate, zinc 3,5-bis(α-methylbenzyl)salicylate, zinc p-toluenesulfonate and zinc 5-butylsalicylate; inorganic acids such as hydrohalic acids (e.g., hydrogen chloride, hydrogen bromide and hydrogen iodide), boric acid, silicic acid, phosphoric acid, sulfuric acid, nitric acid and perchloric acid; and metal halides such as the halides of Al, Zn, Ni, Sn, Ti and B.

Specifically, the recording material of this invention can be produced using the following methods.

Pressure-sensitive copying sheets in accordance with this invention can be produced in various forms as disclosed in the prior art, for example, as disclosed in U.S. Pat. Nos. 2,505,470, 2,505,471, 2,505,489, 2,548,366, 2,712,507, 2,730,456, 2,730,457 and 3,418,250. The chromenoindole color formers in accordance with this invention are dissolved in a solvent either individually or as mixtures thereof, or together with other known color formers, e.g., as disclosed in U.S. Pat. Nos. 2,548,365, 2,548,366, 3,293,060, 3,501,331, 3,506,471, 3,514,310, 3,551,181, 3,631,064, 3,663,571, 3,681,392, 3,697,540, 3,963,553, etc. Examples of suitable solvents which can be used are synthetic oils such as alkylated naphthalenes, alkylated diphenyls, alkylated diphenylmethanes, and alkylated terphenyls; vegetable oils such as cotton seed oil or castor oil; animal oils; mineral oils; and mixtures thereof. The solution is dispersed in a binder, or the solution is encapsulated in microcapsules. The resulting dispersion or the microcapsule dispersion is coated on a support such as paper, a synthetic sheet or a resin-coated paper to form the recording material of this invention.

The amount of the color former is chosen appropriately depending on the desired coating thickness, the form of the pressure-sensitive sheet, the method of preparing the microcapsules and other conditions. Those skilled in the art can easily determine an appropriate amount.

Encapsulation of the color former can be performed using the method based on the coacervation of hydrophilic colloid sols as disclosed in U.S. Pat. No. 2,800,457 and 2,800,458, and the interfacial polymerization method as disclosed in British Pat. Nos. 867,797, 950,443 and 1,091,076.

A general method for producing a thermosensitive recording sheet in accordance with this invention is described below.

A substantially colorless color former, an electron acceptor material and a thermofusible material (used when the color former or the electron acceptor material does not melt at desirable temperatures) are pulverized sufficiently finely, and mixed with a solution or dispersion of a binder in a solvent or a dispersing medium. The mixture is coated on a support such as paper, a synthetic resin sheet, or a resin-coated paper, and dried to form the thermosensitive recording sheet. In preparing the coating mixture, all of the components may be mixed simultaneously and pulverized; or they can be separately pulverized and dispersed as suitable combinations, and then the combinations mixed. Alternatively, the mixed coating dispersion may be added to a support-forming material, and the mixture formed into a sheet. An opacifying agent may be added to the mixture at the time of mixing, if desired.

A thermosensitive recording sheet comprises about 1 to about 2 parts by weight of the color former, about 1 to about 6 parts by weight of the electron acceptor material, 0 to about 30 parts by weight of the thermofusible material, about 1 to about 15 parts by weight of the binder, and about 20 to about 300 parts by weight of the dispersing medium (solvent).

The color former used may be one of the above-described chromenoindole derivatives of the general formula (I) or a mixture of two or more thereof or a mixture of such an chromenoindole with a known color former for a pressure-sensitive copying sheet such as crystal violet lactone or a fluoran derivative. The organic acid or the metal salt thereof described hereinabove is especially suitable for use as an electron acceptor material in this case.

The dispersing medium (solvent) should not substantially dissolve any of the color former and the electron acceptor material. If the dispersing medium dissolves any one of these components, a color would be formed. Accordingly, water is most desirable as the dispersing medium (solvent), and hydrocarbons such as hexane, ligroin and petroleum ether can also be used.

Examples of suitable binders that can be used in this invention include styrene/butadiene copolymers, alkyd resins, poly(butyl methacrylate), vinyl chloride/vinyl acetate copolymers, styrene/maleic anhydride copolymers, synthetic rubbers, gum arabic, polyvinyl alcohol, and hydroxyethyl cellulose.

On considering the dispersing medium (solvent), water-soluble binders such as gum arabic, polyvinyl alcohol and hydroxymethyl cellulose are preferred.

The thermofusible material is a colorless or slightly colored solid at room temperature, and has a sharp melting point at temperatures at which the copying sheets are heated for duplication, namely, about 50° to about 180° C. In the molten state, this material should dissolve at least one, preferably both, of the color former and the electron acceptor material.

Examples of suitable thermofusible materials include acetanilide, urea, diphenylamine, diphenylnaphthalene, benzoin, α-naphthol, β-naphthol, para-t-butylphenol, para-phenylphenol, 4,4'-cyclohexylidine diphenol, 4,4'-isopropylidene diphenol, phthalic anhydride, maleic anhydride, stearic acid, benzoic acid, α-naphthylacetic acid, methyl para-hydroxybenzoate, diphenyl phthalate, triphenyl phosphate, para-hydroxydiphenyl ether, 2,2-bis[4-(β-hydroxyethoxy)phenyl]propane and para-bis(β-hydroxyethoxy)benzene.

Examples of suitable opacifying agents that can be used in this invention are titanium oxide, zinc oxide, barium sulfate, calcium sulfate, and starch.

The electrothermosensitive recording sheet in accordance with this invention can be prepared by dispersing an electrically conductive material, a color former, an electron acceptor material and a binder in a dispersing medium which does not or only scarcely dissolves the color former and the electron acceptor material, and coating the dispersion on a support such as paper; or by first coating the electrically conductive material on the support to form an electrically conductive layer, and then coating a dispersion of the color former, the electron acceptor material, and the binder in water on the electrically conductive layer. Specific procedures are described, for example, in Japanese Patent Application (OPI) Nos. 11344/74 and 48930/75. When the color former and the electron acceptor do not melt at appropriate temperatures (generally about 70° to about 120° C.), their sensitivity to Joule heat generated by the passing of an electric current therethrough can be adjusted by adding a thermofusible material which dissolves at least one of the color former and the electron acceptor material.

Suitable electron acceptor materials and thermofusible material are the same as those described above with regard to the preparation of thermosensitive recording sheets.

The photosensitive recording sheets in accordance with this invention can be prepared by substituting the chromenoindole derivatives of this invention instead of the color formers used in Japanese Patent Publication Nos. 24188/63, 10550/70, 13258/70, 204/74, 6212/74 and 28449/74, and Japanese Patent Applications (OPI) Nos. 32532/73, 31615/72, 9227/74, 135617/74, 80120/75, 87317/75 and 126228/75, such as lactone compounds, lactam compounds, spiropyran compounds, carbinol compounds, ethylene compounds, leucoauramine compounds and oxazine compounds.

Other recording materials can be prepared by using the indolochromene derivatives of this invention instead of conventional color formers.

The following Examples are given to illustrate the present invention in more detail. All parts, percents, ratios and the like in these Examples are by weight, unless otherwise indicated.

EXAMPLE 1

1 part of color former Compound (1) of this invention was dissolved in 30 parts of alkylated naphthalene. With vigorous stirring, the solution was added to 50 parts of water having dissolved therein 6 parts of gelatin and 4 parts of gum arabic to form an emulsion containing oil droplets having a diameter of 1 to 10 microns. Then, 250 parts of water was added thereto. Acetic acid was added little by little to adjust the pH of the dispersion to about 4 thereby to induce coacervation and form a wall of gelatin and gum arabic around the oil droplets. Formaldehyde was added, and the pH of the dispersion was increased to 9 to harden the microcapsule wall.

The resulting microcapsule dispersion was coated on a paper support and dried. When this paper was brought into contact with papers coated respectively with active terra alba, acid terra alba, attapulgite, a phenolic resin, 4,4'-isopropylidene diphenol, zinc 3,5-bis(α-methylbenzyl)salicylate, zinc p-toluenesulfonate and 2,2'-methylenebisphenol, and a pressure or an impact was applied thereto, an image of a blue color was obtained instantly. This image had a high density, and superior fastness to light and heat.

EXAMPLE 2

Pressure-sensitive copying sheets were prepared in the same way as described in Example 1 except that color former Compounds (2) to (12) were used respectively instead of color former Compound (1), and tested in the same way as described in Example 1. Colors of high density were formed rapidly, and the colored letters or images had very good fastness to light and heat.

EXAMPLE 3

30g of color former Compound (3) of this invention was mixed and pulverized for 2 hours with 150 g of a 10% aqueous solution of polyvinyl alcohol (PVA 117, a trade name for a product of Kuraray Co., Ltd.) and 70 g of water to prepare a dispersion. After pulverization, color former Compound (3) had a particle diameter of about 5 microns (Component A).

Separately, 30 g of bisphenol A (4,4'-isopropylidene diphenol), 30 g of acetanilide, 150 g of a 10% aqueous solution of polyvinyl alcohol (PVA 117), and 55 g of water were mixed and pulverized for 2 hours to prepare a dispersion. After pulverization, the insoluble material had a particle diameter of about 5 microns (Component B).

Then, 5 g of Component A was mixed with 40 g of Component B, and the mixture was coated on a paper support and dried to form a thermosensitive recording paper.

When the thermosensitive recording paper was heated to 200° C. using, for example, a hot pen, a dark blue color was formed. When an image-bearing sheet was superimposed on the thermosensitive recording sheet, and the assembly was heated using a thermosensitive copying machine, a dark blue copied image was obtained. The colored images obtained were very stable to light and even when they were exposed to an ultraviolet lamp for 1 hour, scarcely any change in their color shade and density was observed.

EXAMPLE 4

200 parts of cuprous iodide was added to 200 parts of a 1% by weight aqueous solution of polyvinyl alcohol (PVA 117), and the mixture was processed in a ball mill for 24 hours. The resulting dispersion was coated on an art paper using a wire bar, and dried to form an electrically conductive layer.

Then, 35 parts of color former Compound (3) of this invention was added to 400 parts of a 10% aqueous solution of polyvinyl alcohol (PVA 117), and 5 parts of 4,4'-isopropylidene diphenol as an electron acceptor was added. They were processed in a ball mill for 24 hours to form a substantially colorless dispersion. The dispersion was coated on the electrically conductive layer of the art paper using a wire bar which had been so controlled that the resulting coating would have a thickness of about 8 microns. The coating was dried to produce an electrothermosensitive recording sheet.

An AC voltage of 300 V was applied to this recording sheet using a tungsten recording needle electrode with a diameter of 0.25 mm and the recording sheet was scanned at a speed of 540 mm/sec., a recorded image of a blue black color having a reflection density of 0.84 was obtained. The light fastness of this colored image was about 3 times higher than that obtained with crystal violet lactone. When compared with the use of 2-anilino-6-diethylamino-3-methylfluoran, the recorded image had superior light fastness and reduced fog.

EXAMPLE 5

5 g of color former Compound (7) of this invention was dissolved in 50 ml of chloroform, and 40 ml of a 10% benzene solution of polystyrene was added thereto. The mixture was well stirred, and 5 g of carbon tetrabromide was added in a dark place to form a uniform solution. The solution was coated on a polyethylene-coated paper in a dark place, and dried at room temperature.

When the resulting photosensitive paper was exposed to ultraviolet irradiation, a blue color was formed. Subsequent washing with n-hexane fixed the colored image, and the unexposed area did not generate color even when exposed to light for long periods of time.

An image-bearing transparent plastic base was superimposed on the photosensitive paper, and the assembly was exposed to ultraviolet irradiation, a dark blue image with deep and light shades opposite to each other was obtained.

Fog did not form on the photosensitive paper before exposure to light, and the color image formability of the photosensitive paper was very good.

It is particularly noted that the color reactive materials (color formers) disclosed in Japanese Patent Publication No. 24188/63 are greatly inferior to the chromenoindole derivatives of this invention in regard to the formation of fog before exposure, and in regard to the light fastness and optical density of the formed color images.

EXAMPLE 6

Using the Compounds (1) and (9) of this invention instead of conventional color formers, the procedures described in Example 1 of each of the patents shown below were repeated to produce an ultrasonic recording sheet (French Pat. No. 2,120,022), an electron beam recording material, a colored image on a photosensitive material for plate making (Japanese Patent Application (OPI) No. 12104/73), an impression-stamping material (Japanese Patent Publication No. 10766/72), a typewriter ribbon (Japanese Patent Application (OPI) No. 3713/74), a ball-point pen ink (Japanese Patent Application (OPI) No. 83924/73) and a crayon (U.S. Pat. No. 3,769,045). All materials gave colored images having superior light fastness.

EXAMPLE 7

Microcapsule dispersions were prepared in the same way as described in Example 1 using the following comparative conventional color former compounds (a) and (b) and the Compound (1) of the present invention.

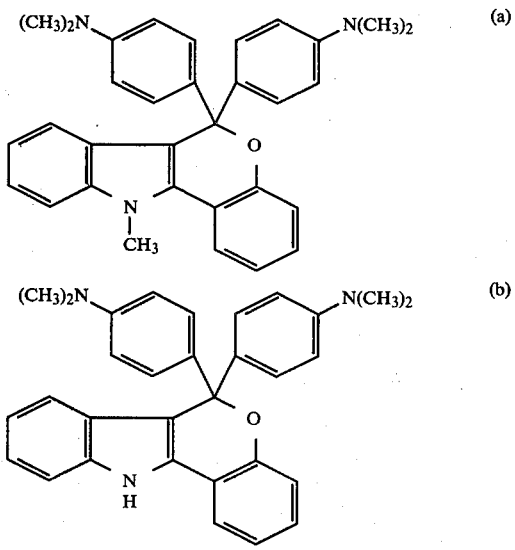

The resulting microcapsule dispersion was coated on a paper support respectively and dried to give Samples (A), (B) and (C) shown in the following Table 1.

The color density of each sample measured using a reflection color densitometer was shown in Table 1. This value shows the degree of the undesirable color formation occurred during encapsulation.

Further, each sample was given pressure uniformly, then the color density was measured. This value shown in Table 1 shows the fogging of the sample.

TABLE 1

| | Color Former Used | The Degree of Color Formation during Encapsulation | The Degree of Fogging |
|---|---|---|---|
| Sample A | Compound (a) (comparision) | 0.36 | 0.38 |
| Sample B | Compound (b) (comparision) | 0.32 | 0.35 |
| Sample C | Compound (1) (present invention) | 0.12 | 0.15 |

It is apparent from the data shown above that the color former compound of the present invention shows the excellent properties comparing the comparative conventional color former compounds.

While the invention has been described in detail and with reference to specific embodiments thereof, it will be apparent to one skilled in the art that various changes and modifications can be made therein without departing from the spirit and scope thereof.

What is claimed is:

1. A pressure-sensitive recording material comprising a support having thereon a layer of microcapsules containing at least one chromenoindole derivative color former which is capable of forming a color upon contact with an electron acceptor material and which is represented by the following general formula (I):

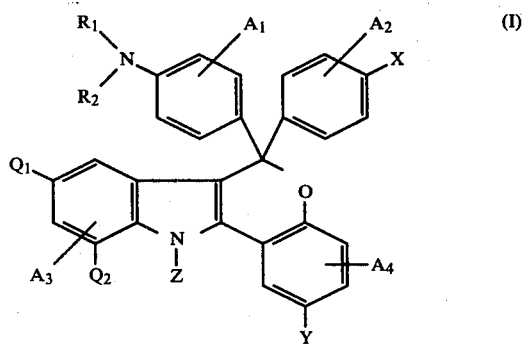

wherein $R_1$ and $R_2$, which may be the same or different, each represents an alkyl group, an alkyl group substituted with one or more of a cyano group, a halogen atom or an alkoxy group, an aralkyl group, a phenyl group or a phenyl group substituted with one or more of an alkyl group or a halogen atom; X represents a hydrogen atom, an alkoxy group, a dialkylamino group, an alkylarylamino group, an alkylaralkylamino group, a diaralkylamino group, an acylamino group, a halogen atom or an alkyl group; Y represents a hydrogen atom, an alkyl group, a halogen atom, an alkoxy group or a nitro group; Z represents an acyl group, a carbamoyl group, an alkoxycarbonyl group, a sulfamoyl group or a sulfonyl group; $Q_1$ and $Q_2$, which may be the same or different, each represents a hydrogen atom, a lower alkyl group or a halogen atom; and $A_1$, $A_2$, $A_3$ and $A_4$, which may be the same or different, each represents a halogen atom, an alkyl group or an alkoxy group.

2. A pressure-sensitive recording material comprising a layer of an electron acceptor material as a color developer and a layer of microcapsules containing at least one chromenoindole derivative color former which is capable of forming a color upon contact with an electron acceptor material and which is represented by the following general formula (I):

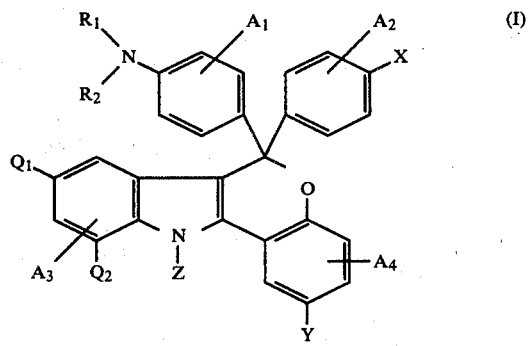

wherein $R_1$ and $R_2$, which may be the same or different, each represents an alkyl group, an alkyl group substituted with one or more of a cyano group, a halogen atom or an alkoxy group, an aralkyl group, a phenyl group or a phenyl group substituted with one or more of an alkyl group or a halogen atom; X represents a hydrogen atom, an alkoxy group, a dialkylamino group, an alkylarylamino group, an alkylaralkylamino group, a diaralkylamino group, an acylamino group, a halogen atom or an alkyl group; Y represents a hydrogen atom, an alkyl group, a halogen atom, an alkoxy group or a nitro group; Z represents an acyl group, a carbamoyl group, an alkoxycarbonyl group, a sulfamoyl group or a sulfonyl group; $Q_1$ and $Q_2$, which may be the same or different, each represents a hydrogen atom, a lower alkyl group or a halogen atom; and $A_1$, $A_2$, $A_3$ and $A_4$, which may be the same or different, each represents a halogen atom, an alkyl group or an alkoxy group.

3. The recording material of claim 1, wherein Z represents an alkylcarbonyl group, an arylcarbonyl group, an alkoxycarbonyl group, a carbamoyl group, an alkylsulfonyl group, an arylsulfonyl group or a sulfamoyl group.

4. The recording material of claim 2, wherein Z represents an alkylcarbonyl group, an arylcarbonyl group, an alkoxycarbonyl group, a carbamoyl group, an alkylsulfonyl group, an arylsulfonyl group or a sulfamoyl group.

5. The pressure-sensitive recording material of claim 1, wherein said support is paper, a synthetic resin sheet or a resin-coated paper.

6. The pressure-sensitive recording material of claim 2, wherein said support is paper, a synthetic resin sheet or a resin-coated paper.

7. The pressure-sensitive recording material of claim 1, wherein said color former represented by the general formula (I) is:

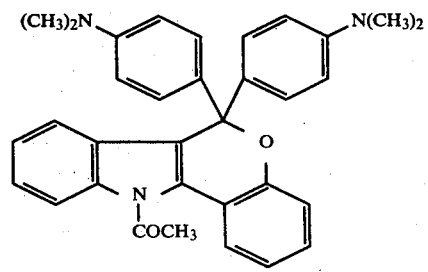

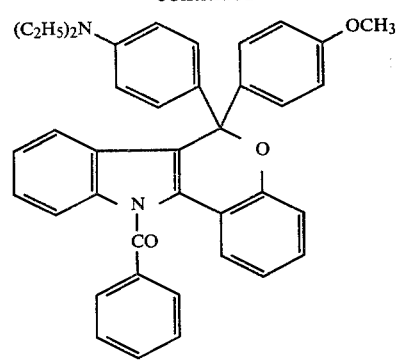
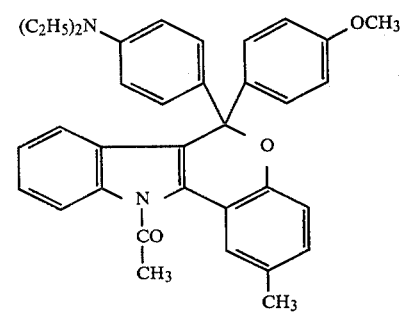
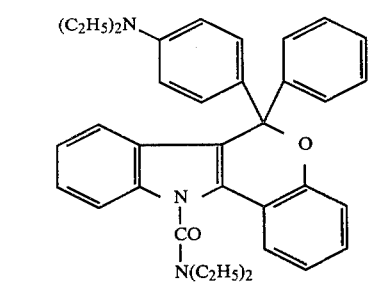
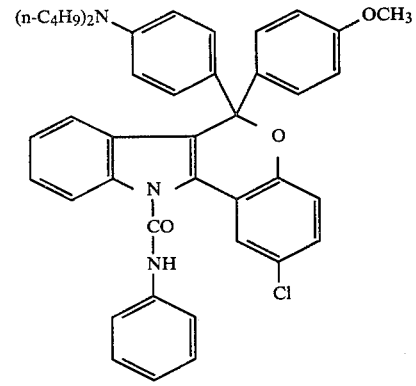
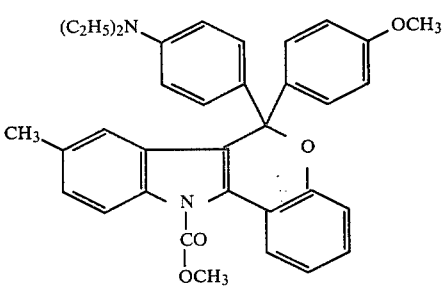
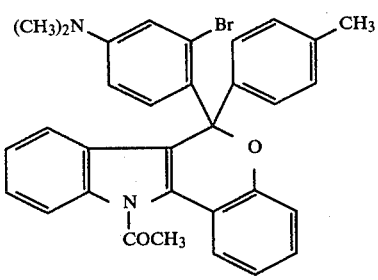
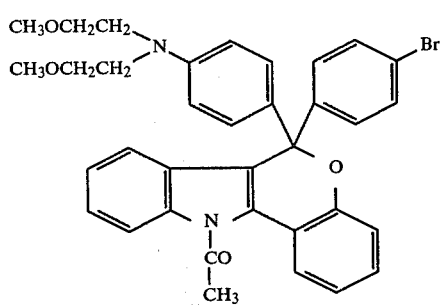
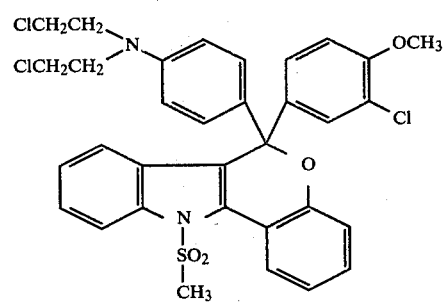
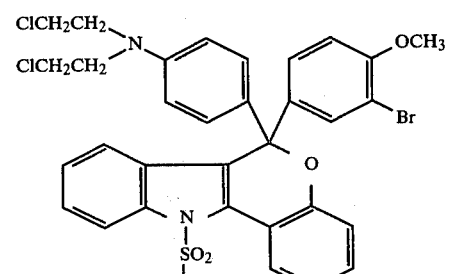
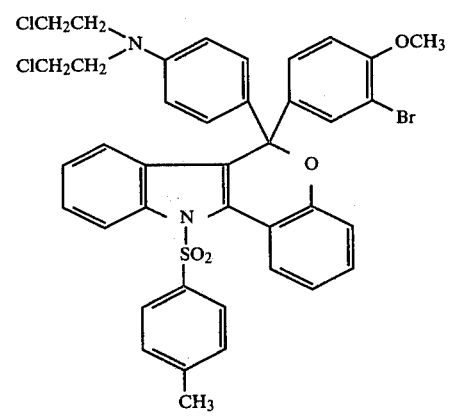
or

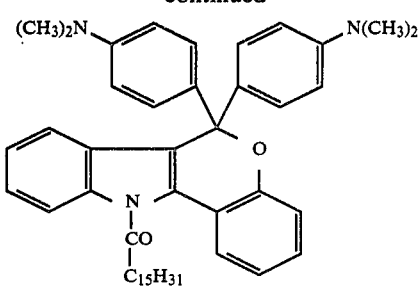
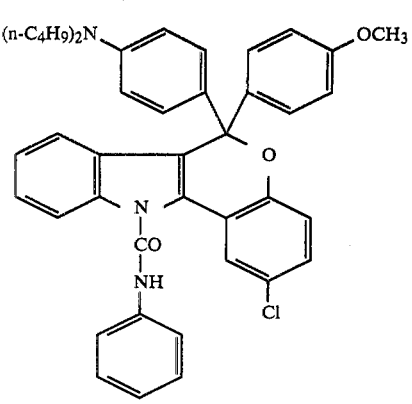
8. The pressure-sensitive recording material of claim 2, wherein said color former represented by the general formula (I) is:
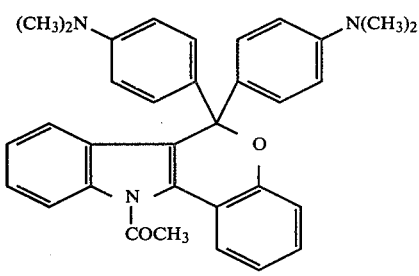
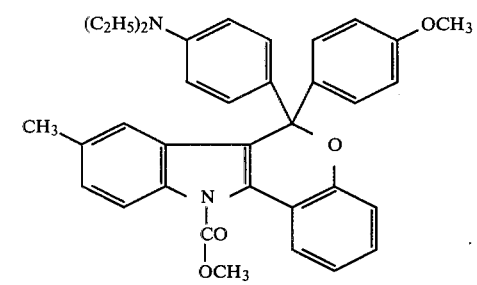
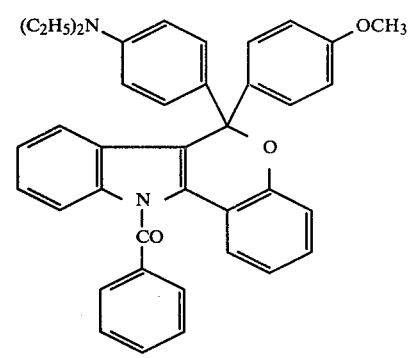
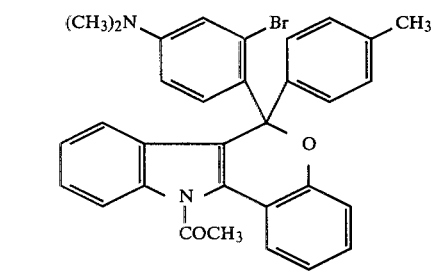
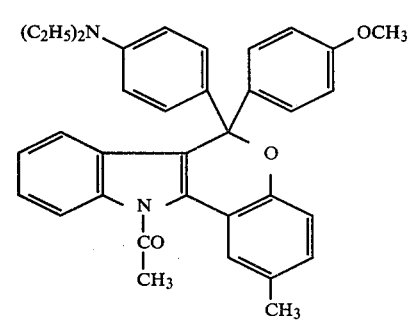
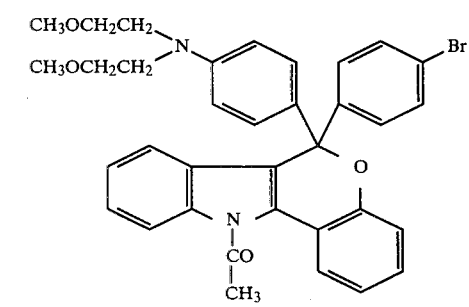
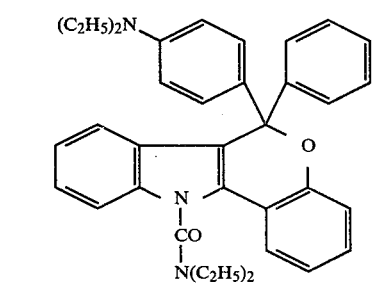
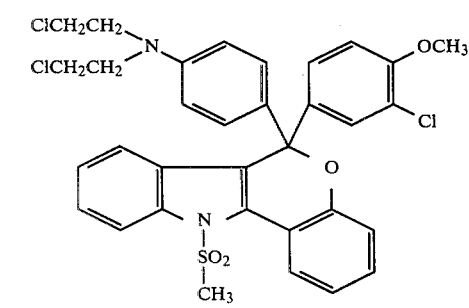

-continued

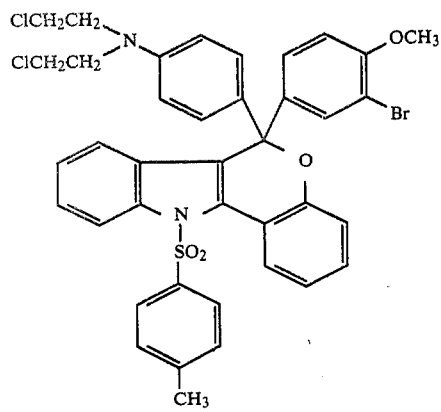

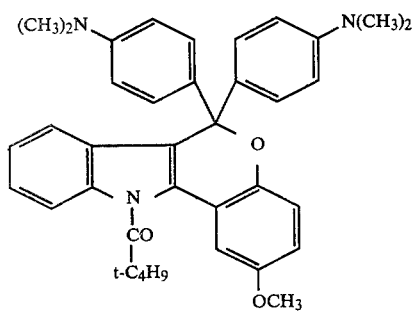

or

-continued

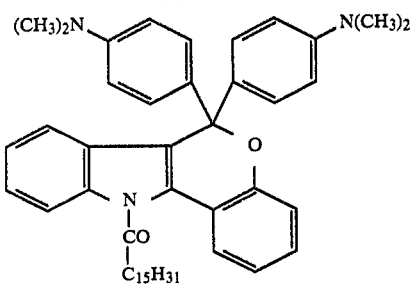

9. The pressure-sensitive recording material of claim 2, wherein said electron acceptor material is selected from the group consisting of a clay mineral, a phenol, a phenolic resin, an organic carboxylic or sulfonic acid, a metal salt of an organic acid, an inorganic acid or a metal halide.

10. The pressure-sensitive recording material of claim 9, wherein said electron acceptor material is selected from the group consisting of active terra alba, acid terra alba, attapulgite, montmorillonite, p-phenylphenol, o-phenylphenol, o-ethylphenol, p-ethylphenol, p-butylphenol, 2,4-dibutylphenol, o-cresol, m-cresol, p-cresol, o-chlorophenol, p-chlorophenol, o-benzylphenol, p-benzylphenol, xylenol, thymol, resorcinol, hexylresorcinol, α-naphthol, β-naphthol, 4,4'-isopropylidene diphenol, 2,2'-methylenebisphenol, aluminum 3,5-dibutylsalicylate, zinc 3,5-dibutylsalicylate, zinc 3,5-bis(α-methylbenzyl)salicylate, zinc p-toluenesulfonate, zinc 5-butylsalicylate, hydrogen chloride, hydrogen bromide, hydrogen iodide, boric acid, silicic acid, phosphoric acid, sulfuric acid, nitric acid, perchloric acid or a metal halide of Al, Zn, Ni, Sn, Ti or B.

11. The recording material of claim 1, wherein Z represents an acyl group.

12. The recording material of claim 2, wherein Z represents an acyl group.

* * * * *